US008925809B2

(12) United States Patent
Bossoney et al.

(10) Patent No.: US 8,925,809 B2
(45) Date of Patent: Jan. 6, 2015

(54) KEY-CARD ACCESS SYSTEM FOR PROVIDING SELECTIVE ACCESS TO MEDICAL EQUIPMENT

(75) Inventors: Luc Bossoney, Villars-Burquin (CH); Benito Valencia Avila, Saillon (CH); Blaise Paratte, Colombier (CH)

(73) Assignee: Codman Neuro Sciences SARL (CH)

( * ) Notice: Subject to any disclaimer, the term of this patent is extended or adjusted under 35 U.S.C. 154(b) by 1470 days.

(21) Appl. No.: 12/254,405

(22) Filed: Oct. 20, 2008

(65) Prior Publication Data

US 2010/0096451 A1    Apr. 22, 2010

(51) Int. Cl.
*G06K 5/00* (2006.01)
*G07C 9/00* (2006.01)
*A61N 1/372* (2006.01)
*G06K 7/08* (2006.01)
*G06K 19/06* (2006.01)

(52) U.S. Cl.
CPC ........ *G07C 9/00896* (2013.01); *A61N 1/37264* (2013.01); *G06K 7/082* (2013.01); *G06K 19/06196* (2013.01); *G07C 9/00738* (2013.01)
USPC ............................ 235/382; 235/449; 235/493

(58) Field of Classification Search
USPC ......... 235/375, 380, 382, 435, 439, 440, 449, 235/487, 493
See application file for complete search history.

(56) References Cited

U.S. PATENT DOCUMENTS 3,415,087 A    12/1968  Kramasz
3,634,657 A *   1/1972  Ballard et al. ................ 235/449

(Continued)

FOREIGN PATENT DOCUMENTS

GB         2026081 A       1/1980
WO      WO 0143821 A1     6/2001
WO    WO 2008005843 A2    1/2008

OTHER PUBLICATIONS

European Search Report EP09252445.3 dated Mar. 5, 2013.

*Primary Examiner* — Paultep Savusdiphol (57) ABSTRACT

An access system for controlling access of a user to one of several unique operative modes of an electronic device used to communicate with an implantable medical device. The access system includes a portable keycard, which is held by a user. The keycard has embedded magnets arranged in a unique predetermined pattern. The electronic device has a housing that provides a slot and a channel for receiving the keycard by the user. A sensing circuit and a processing circuit are both provided. The sensing circuit includes Hall-effect transducers positioned next to the channel so that upon inserted of the keycard, certain ones of these Hall-effect transducers will reside adjacent a magnet, depending on the particular unique pattern. A magnet positioned adjacent a Hall-effect transducer will cause the transducer to send an output signal to the processor indicating the presence of a magnet at the location of the Hall-effect transducer. The Hall-effect transducers collectively generate an electronic pattern representing the particular identity of the keycard. The processor compares this electronic pattern with one of several stored in electronic memory and provides selective access to the device in response to successfully identifying a match. A doctor, a technician, a salesperson and a factory assembly worker are examples of users of this system and each will be granted predetermined access rights to operate the device. Additional Hall-effect transducers may be provided to help detect the intrusion of magnetic fields produced from magnets not located with the keycard. The process will deny any access to the device should any such remove magnetic fields be detected.

32 Claims, 6 Drawing Sheets

(56) References Cited

U.S. PATENT DOCUMENTS

| | | | |
|---|---|---|---|
| 3,701,126 A * | 10/1972 | Reichard | 365/9 |
| 3,790,957 A | 2/1974 | Dukes et al. | |
| 3,896,292 A * | 7/1975 | May et al. | 235/450 |
| 3,953,712 A * | 4/1976 | Horvath | 235/449 |
| 4,004,134 A * | 1/1977 | Hwang | 235/431 |
| 4,112,292 A * | 9/1978 | Varvel et al. | 235/449 |
| 4,130,242 A * | 12/1978 | Mannion | 235/450 |
| 4,213,039 A * | 7/1980 | Schasser | 235/449 |
| 4,253,017 A * | 2/1981 | Whitehead | 235/449 |
| 4,257,030 A * | 3/1981 | Bruhin et al. | 340/5.65 |
| RE31,211 E * | 4/1983 | Whitehead | 235/449 |
| 4,414,831 A * | 11/1983 | Perkut | 70/276 |
| 4,507,944 A | 4/1985 | Widen et al. | |
| 4,585,930 A * | 4/1986 | Casden | 235/449 |
| 4,629,875 A * | 12/1986 | Uemura | 235/450 |
| 4,727,368 A | 2/1988 | Larson et al. | |
| 4,777,815 A | 10/1988 | Lovell et al. | |
| 4,979,383 A | 12/1990 | Tully | |
| 5,455,571 A | 10/1995 | Janssen | |
| 6,097,306 A | 8/2000 | Leon et al. | |
| 6,122,580 A | 9/2000 | Autermann | |
| 6,317,025 B1 | 11/2001 | Leon et al. | |
| 6,809,636 B2 | 10/2004 | Metlitzky et al. | |
| 6,822,552 B2 | 11/2004 | Liden et al. | |
| 6,903,318 B2 | 6/2005 | Thorneywork | |
| 2005/0099265 A1 | 5/2005 | Dix et al. | |

* cited by examiner

KEY-CARD ACCESS SYSTEM FOR PROVIDING SELECTIVE ACCESS TO MEDICAL EQUIPMENT

BACKGROUND OF THE INVENTION

1) Field of the Invention

The present invention generally relates to controlled access systems for controlling the access to select users of equipment, and more particularly, to magnetic-based key access systems for controlling the access to select users of medical equipment.

2) Discussion of Related Art

Magnetically encoded cards have been used successfully for years to help control access to machines, doors, and locks. So called magnetic locks were originally mechanical locking devices. This type of lock includes magnetically controllable tumblers. A magnetic key used with this lock has embedded therein permanent magnets arranged in a prescribed pattern. If the pattern of the magnets within the key match the combination of the lock, the fields of each magnet exactly align with the tumblers of the lock. The field strength and field orientation of each aligned magnet within the "correct" key causes the tumblers to displace to a mechanically-open position. The tumblers of the lock are spring-biased and the magnets displace each tumbler against the action of each spring. The spring bias returns each tumbler to the locked position when the key is removed. Furthermore, if the device being controlled is electric, then an appropriate electric switch operating the device becomes moveable only when the tumblers move to an open position.

One benefit of this type of magnetic key locking system is that a typical key-slot or keyhole is not required to actuate the lock. The lock may be designed so that the magnetic key need only be positioned against a surface that lies adjacent to the tumblers of the lock. This is a great benefit for use in corrosive areas or areas where environmental conditions do not favor the delicate tumbler mechanisms of a lock. Also, if the tumblers are not physically accessible, they cannot be picked in a traditional manner, making this type of lock system more secure than conventional locks.

Unfortunately, mechanical locks have their limitations. Disadvantages include the expense of manufacture and the fact that many applications for this type of lock are electrically controlled, such as computer equipment, electrical medical devices, lighting, etc. The latter disadvantage led to the development of a magnetically-operated lock that uses electronic magnetic-field detecting devices which effectively replace the mechanical tumblers used in earlier lock versions, described above. Such magnetic-field detecting devices include reed switches and more reliable, more accurate and durable Hall effect sensors in an IC package.

A Hall effect sensor is a well known electronic device that can be used to detect the presence of a magnetic field. The Hall effect refers to the potential difference (Hall voltage) on the lateral sides of an electrical conductor crossed by an electric current when a magnetic field is applied perpendicularly. By measuring the lateral voltage potential, the strength and field orientation of the adjacent magnet can be determined. Such Hall effect sensors can be used to measure very small and slow fluctuations in a magnetic field, down to a hundredth of a gauss.

With the introduction of electronic magnetic-field sensing devices, key-card controlled access systems could be more reliable, less expensive and provide a greater number of key-combinations than with the above-described magnetically-controlled mechanical tumbler security system. The electronic magnetic-field sensors can also more directly and more reliably control the electronic security device whose access is being controlled.

Such key-access systems using electronic magnetic-field sensing devices generally provide consistent, accurate and reliable use and are generally durable in many different types of harsh environments, except one-magnetic environments.

On a regular basis, hospitals and clinics use a variety of electronic devices, many of which emit strong electromagnetic energy. Such strong-emitting devices include MRI units, monitors and defibrillators. Unless property shielded, these and almost every electronic device used everyday within the medical environment emits a certain amount of electromagnetic energy. The emitted electromagnetic energy creates weak and strong magnetic fields which can affect the operation of other electronic devices operating nearby. One type of device that could easily be affected by these fields is magnetically-controlled access systems which are relying on magnetic-field sensing components. Even relatively weak magnetic fields could interfere with the operation of the Hall-effect sensors and thereby prevent the access control device from accurately reading a key card. This magnetic interference could either provide improper access to an unauthorized user or prevent access to legitimate users.

It is a first object of the present invention to provide an access control system that overcomes the deficiencies of the prior art.

It is a second object of the present invention to provide an access control system that allows an authorized individual access to select and predetermined mode of operation to an electrical device.

It is another object of the present invention to provide an access control system that includes provisions to control and mitigate the effects of any outside interference caused by nearby electromagnetic fields.

SUMMARY OF THE INVENTION

An access system for controlling access of a user to one of several unique operative modes of an electronic device used to communicate with an implantable medical device. The access system includes a portable keycard which is held by a user. The keycard has embedded magnets arranged in a unique predetermined pattern. The electronic device has a housing that provides a slot and a channel for receiving the keycard by the user. A sensing circuit and a processing circuit are both provided. The sensing circuit includes Hall-effect transducers positioned next to the channel so that upon inserted of the keycard, certain ones of these Hall-effect transducers will reside adjacent a magnet, depending on the particular unique pattern. A magnet positioned adjacent to a Hall-effect transducer will cause the transducer to send an output signal to the processor indicating the presence of a magnet at the location of the Hall-effect transducer. The Hall-effect transducers collectively generate an electronic pattern representing the particular identity of the keycard. The processor compares this electronic pattern with one of several stored in electronic memory and provides selective access to the device in response to successfully identifying a match. A doctor, a technician, a salesperson and a factory assembly worker are examples of users of this system and each will be granted predetermined access rights to operate the device. Additional Hall-effect transducers may be provided to help detect the intrusion of magnetic fields produced from magnets not located with the keycard. The process will deny any access to the device should any such remove magnetic fields be detected.

BRIEF DESCRIPTION OF THE DRAWINGS

The invention can be more fully understood from the following detailed description taken in conjunction with the accompanying drawings, in which.

DETAILED DESCRIPTION OF THE PREFERRED EMBODIMENTS

By way of introduction, the present invention is a keycard-controlled-access system that receives one of several keycards at a time and includes a keycard holder, sensors for reading an inserted keycard and a processing circuit for determining access in response to the outputs of the sensors. This invention is meant to be included into the design of any of a variety of electronic devices used in a medical environment to which access is to be controlled. However, the present invention is most suited for such electronic medical devices that are mobile (such as handheld devices) because these devices are more likely to experience stray magnetic fields from other electronic sources as the device is moved throughout the hospital or clinic.

Although the present invention can easily be adapted to many different types of electronic medical equipment, it is preferably incorporated into a portable control unit that is used to communicate with and control the operation of an implanted infusion pump, pace maker or any other implanted device that requires RF communication and control from a remote device. This control unit includes an RF antenna, controlling and processing circuitry, a keypad for entering data and a display for reading data, and also a key slot into which the above introduced keycard is inserted by authorized personnel. As can be appreciated by those skilled in the art, the keycard holder, reading and processing circuitry, and the above listed components are enclosed or mounted to a housing that is not described or shown in any great detail in the immediate application since such details are considered beyond the scope of this invention. Only the above-described main components are shown to help explain the structure and operation of the invention.

Keycard

Figure 1:
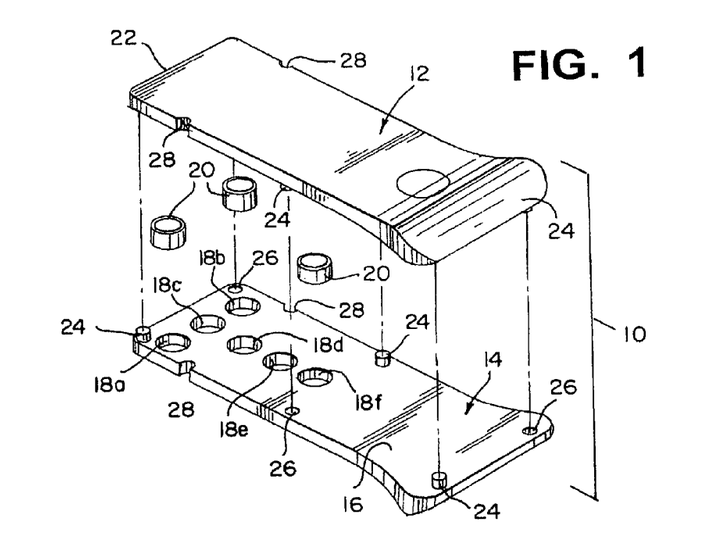
FIG. 1 is a perspective assembly view of a key card according to a first embodiment of the invention including a top section, a bottom section, and several magnets used to form a key combination.

Referring to FIG. 1 an assembly view of a key card 10 is shown according to a first embodiment of the invention, including a top section 12 and a bottom section 14. The two sections 12, 14 are preferably made from a strong durable plastic, manufactured by an injection molding process. Top section 12 and bottom section 14 are sized and shaped to mate with each other at a common plane 16 and will eventually (after assembly) be bonded to each other at this plane using either an appropriate adhesive or preferably hermetically bonded using an ultrasonic welding process. To aid in manufacturing, top section 12 and bottom section 14 are preferably identical.

According to this first embodiment of the invention, both top section 12 and bottom section 14 include several bores 18a-18f. Bores 18a-18f of top section 12 are positioned to align with the corresponding bores 18a-18f of bottom section 14 when the two sections are mated to each other. The combined bores 18a-18f are each sized and shaped to snugly receive a magnet 20. Bores 18a-18f are preferably cylindrically shaped so that the combined bores can receive a cylindrically shaped permanent magnet. The magnets are preferably press-fit into their respective bore 18a-18f or bonded therein using an appropriate adhesive in such a manner that prevents magnets 20 from moving or rotating from within their bore.

In the example shown in the figures, the keycard 10 includes six bores 18a-18f that are arranged in the shape of a "T" with two "corner" bores 18a and 18b being located at the two corners of a front edge 22 of the generally rectangular keycard 10 and four axial bores 18c, 18d, 18e and 18f being positioned perpendicular to front edge 22 and extending down the middle of the keycard, as shown in FIG. 1. This particular arrangement is just one example used to explain the present invention. It should be understood that many other different bore arrangements (and therefore magnet arrangements) can be used to increase the possible key permutations. Also, the number of bores can be increased or decreased as necessary, depending on the particular application and the required number of unique key combinations. As describe below, magnets 20 located within corner bores 18a, 18b are used to provide initial announcement to the controlling circuitry that a keycard 10 is being inserted into the device and also to indicate when the keycard reaches the fully inserted position. Bores 18c, 18e and 18f are combination bores and are reserved for encoding the keycard 10 with a unique code. Magnets 20 are selectively arranged in these combination bores during assembly following a prescribed order. The "combination" or unique identity of the keycard is determined by which ones of the three combination bores 18c, 18e and 18f are supplied with a magnet.

As introduced above, the present invention is intended to be incorporated into a particular type of medical device, a control unit that is used to communicate and control an implantable medical device. This particular application only requires a limited number of different key combinations. In this first embodiment, different key combinations are determined by the number of magnets inserted into the three "combination" bores 18c, 18e, and 18f, and which of the four bores 18c-f are used.

As shown in FIG. 1, top section 12 and bottom section 14 each include integrally-formed alignment pins 24 and mating bores 26 which are both used to help register the two sections 12, 14 together when bonded. Also, each section 12, 14 includes a notch 28 located along each side edge 30 of each section 12, 14, which align to form a common notch 28 on each side of the assembled keycard 10. These notches are used to help hold the keycard 10 into a fully inserted position with respect to reading circuitry, described in greater detail below.

According to this exemplary application, the control unit used to communicate with and control the operation of an implanted device requires just four keycards 10, each with a unique combination. One keycard 10 is intended for use by a physician, a second one is intended to be used by a technician, a third by a salesman, and finally, a fourth one is meant to be used by an assembly worker in the factory that manufactures the device. If no key is inserted into the control unit, the control unit will operate in a "patient" mode. In each case, a level of access to the different features and data is provided, according to the particular access required by that user to perform their particular task while using the control unit.

The magnet combinations which determines the unique code or identity of the particular keycard is established before top section 12 and bottom section 14 are bonded to each other. Once keycard 10 is bonded, the combination cannot be changed. Since only four key combinations are required for this particular exemplary application, the specific magnet arrangement for each key combination can be designed to mitigate misreads by the sensors during use so that a keycard meant for the doctor will never be misread by the sensors and circuitry as a salesman keycard, etc.

Keycard Holder

Figure 2:
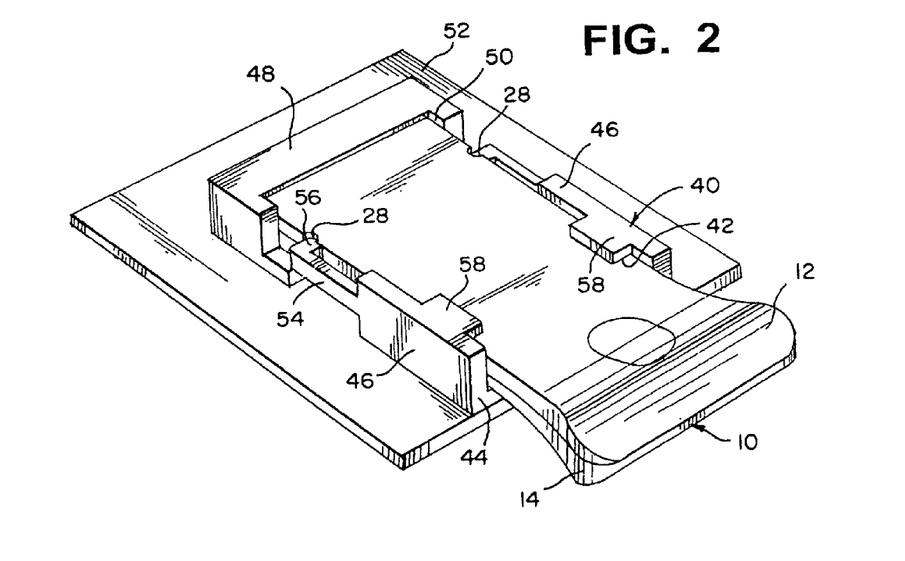
FIG. 2 is a perspective view of a key holder attached to a printed circuit board and showing a key card located in a fully inserted position, according to the first embodiment of the invention.
Figure 3:
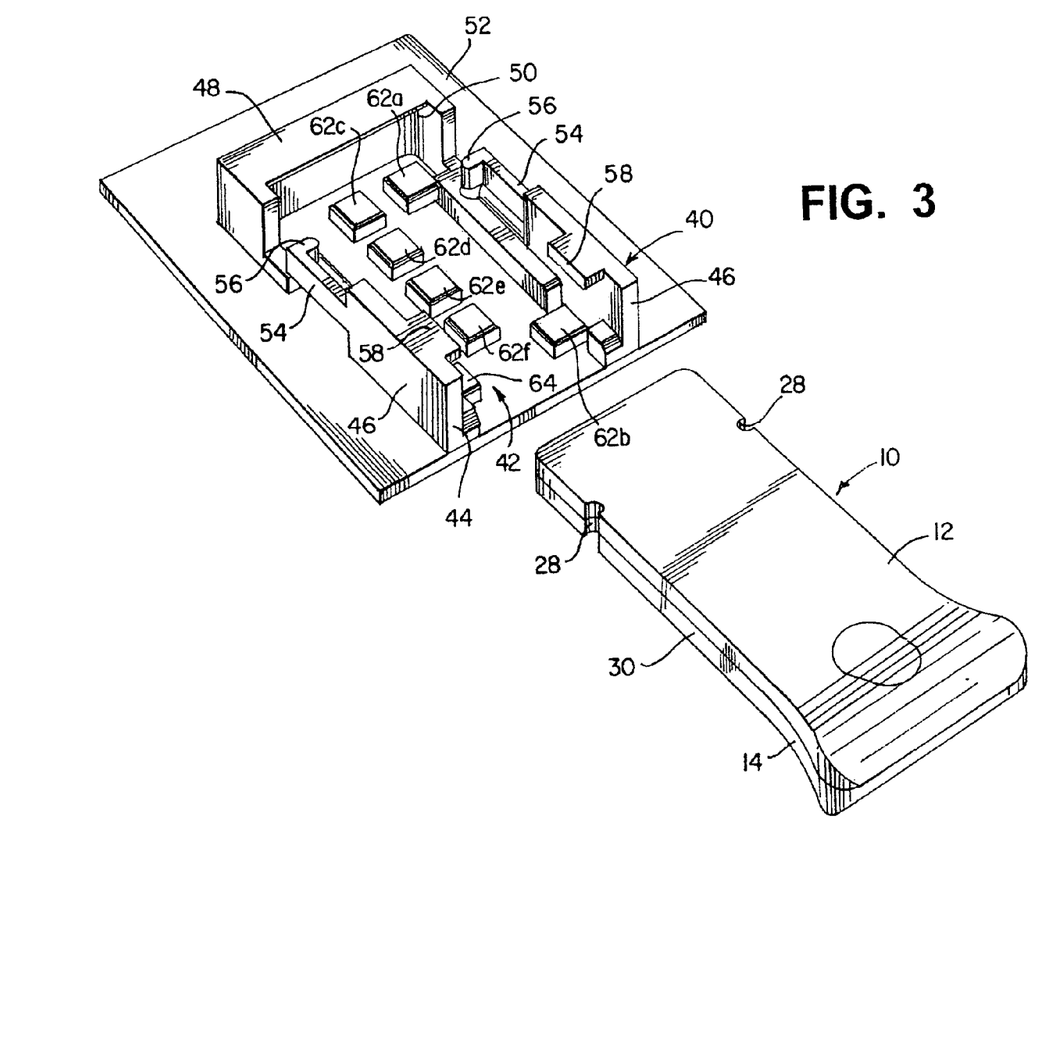
FIG. 3 is a perspective view of the key receiver and key card of FIG. 2 located in a fully removed position, showing details of a mechanical locking tab and the Hall effect sensors, according to the first embodiment of the invention.

Referring now to FIG. 2, a keycard holder 40 is shown with a keycard 10 in a fully inserted position. Referring now to FIGS. 2 and 3, as described below, keycard holder 40 is a simple open-frame structure that includes an accessible slot 42 at a front end 44 that is sized and shaped to receive keycard 10 and has two side walls 46 and an end wall 48. Together, this structure defines an appropriately sized and shaped channel 50 into which keycard 10 may freely slide after being inserted into slot 42. The purpose of keycard holder 40 is to receive and firmly hold an inserted keycard 10 so that adjacent circuitry and sensors can "read" the magnet key combination and actuate the control unit (or other electronic device) accordingly.

Keycard holder 40 is preferably made from plastic using an appropriate injection molding process and includes projections (not shown here) so that it can be firmly secured to a printed circuit board 52. Keycard holder 40 includes integrally formed spring-biased locking arms 54 on each side 46. Each arm 54 includes a locking tab 56 which is sized and shaped to align and engage with notch 28 of keycard 10 when keycard 10 reaches its fully inserted position. As is understood by those skilled in the art, spring arms 54 provide a spring-bias based on the resiliency of the material used to make the keycard holder 40 and certain dimensional factors, which forces each respective locking tab 56 inwardly into contact with the respective side edges 30 keycard 10 as keycard slides within channel 50 to its fully inserted position. The engagement between locking tabs 56 and notches 28 is strong enough to effectively hold keycard 10 in place during use, but this engagement is meant to be easily overcome by the user when so desired, by merely pulling out the keycard 10. As shown in FIGS. 2 and 3, keycard holder 40 further includes appropriate overhang tabs 58 to help guide and hold keycard 10.

Control Unit

Figure 4:
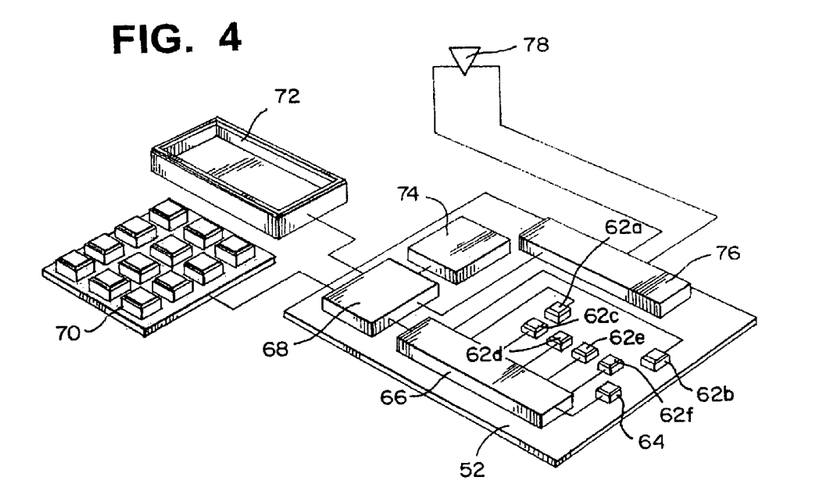
FIG. 4 is a perspective view of the basic components of an exemplary medical device that incorporates the access control system of FIG. 3 and further includes an antenna, a display, an input interface, a memory circuit, a processor circuit and a sensor interface circuit, and showing the layout of several Hall-effect sensors, according to the first embodiment of the invention.
Figure 5:
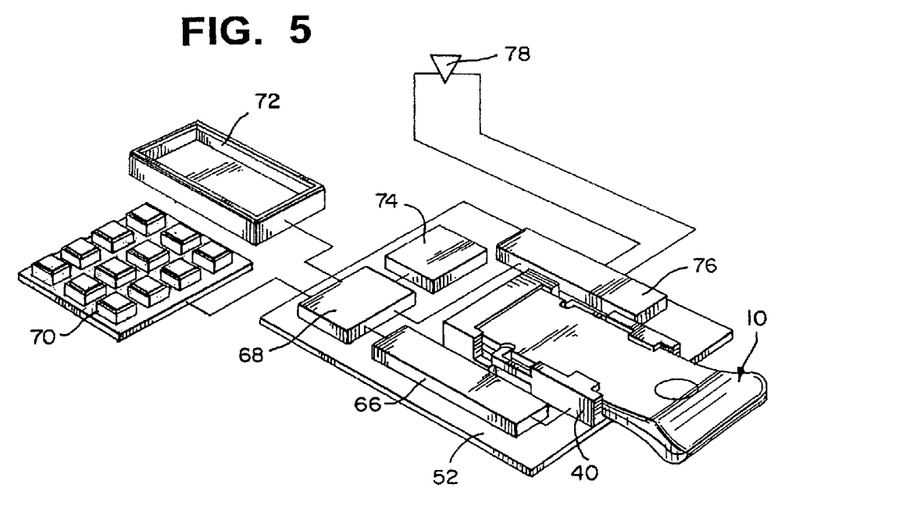
FIG. 5 is a perspective view of the basic components of the device of FIG. 4, furthering including the key-holder of FIG. 2 and showing a key card in the fully inserted position, according to the first embodiment of the invention.

Referring now to FIGS. 4 and 5, the main components of a control unit 60 are shown as an exemplary application of the access system of the present invention. Control unit 60 includes circuit board 52 (introduced above and in FIGS. 2 and 3) including several Hall-effect sensors—a "start" sensor 62b, a stop sensor 62a, three "combination" sensors 62c, 62d and 62f and at least one reference sensor 64, but preferably three reference sensors, 64, 62b and 62e. Sensors 62a-f and reference sensor 64 are each electrically connected to a sensor interface IC chip 66 which includes an analog to digital converter and other known electronic logic components and is used to read and process the voltage readings of each of the seven Hall-effect sensors 62a-f, 64 and send either a "high" or a "low" signal to the processor 68. The sensor interface IC chip 66 is connected to a processor chip 68. Also connected to processor 68 is a keypad input 70, a display 72, a memory chip 74 and an RF antenna interface chip 76, which includes known circuitry to help receive, transmit and process RF signals, as instructed by processor chip 68. An antenna 78 is electrically connected to antenna interface chip 76 so that RF signals may be transmitted to and received from the implanted device located within a nearby patient.

The above-described components of control unit 60 are introduced here only to help explain the operation of the present invention. Not all of these components are described in great detail because such details are beyond the scope of this invention. Also, keycard holder 40 and the keycard 10 are not shown in FIG. 4 so that the details of Hall-effect sensors 62a-f, 64 may be revealed. FIG. 5 shows the same components as shown in FIG. 4 with the addition of keycard holder 40 and a keycard 10 inserted therein.

As described above, it is not uncommon in medical environments, such as hospitals for electronic devices to experience stray magnetic fields. This is a concern with the present device since the above-described control unit relies on carefully positioned magnet fields to unlock and provide operational access to the device by select personnel. To help eliminate or at least mitigate the adverse effects of any incoming stray magnetic fields entering control unit 60, reference sensors 64, 62b and 62e are provided within the array of sensors 62a-f on circuit board 52. Reference sensor 64 is used to read the magnetic field present in the immediate vicinity of sensors 64, 62b and 62e. These three reference sensors are logically wired so that during use, if any of the three reference sensors 64, 62b and 62e detects a magnetic field above a certain predetermined threshold value, the sensor that detects the field will send a logic low (effectively change its output signal) to processor 68 which will prevent the card from being read.

In operation, as described below, when a keycard 10 is being "read" by combination sensors 62c, 62d and 62f, their respective output voltages will be converted into digital high and low signals and sent to processor 68. Processor will then "read" the logic outputs of reference sensors 64, 62b and 62e. If any or more of these reference sensors are found to be at a logic low, then processor will postpone reading the combination sensors 62c, 62d and 62f because in this example, a magnetic field outside the device is influencing onboard components. In this manner, detection of stray magnetic fields generated by magnets other than the magnets located on keycard 10 will prevent the reading of an inserted keycard 10. Since such stray magnetic fields could cause processor 68 to misread the "combination" of keycard 10, when any stray magnetic fields are detected, it is preferred that processor 68 does not provide any access to the medical device. Reference sensors 64, 62b, and 62e are preferably only operational when keycard 10 is being "read" by control unit 60.

As introduced above, combination sensors 62c, 62d and 62f, start sensor 62b and stop sensor 62a are provided on circuit board 52 in a predetermined pattern and are positioned to be immediately adjacent to keycard 10 when the keycard is inserted into slot 42 and along channel 50 of keycard holder 40. Sensors 62a-f should be positioned as close to keycard 10 as possible to help ensure accurate reading of an inserted keycard. As described in greater detail below, as the keycard is further inserted into the slot 42, eventually either of the two corner magnets will move immediately adjacent to stop sensor 62a. When this sensor moves to a "low" state, it means that the sensor 62a detected the magnetic field of the magnet indicating that the keycard is now fully inserted into slot 42 and that processor 68 should interrogate the reference sensors 64, 62b and 62e to determine their respective state. If the state of those reference sensors remains at a high state, processor 68 can then proceed to summon the state of combination sensors 62c, 62d and 62f.

Figure 6:
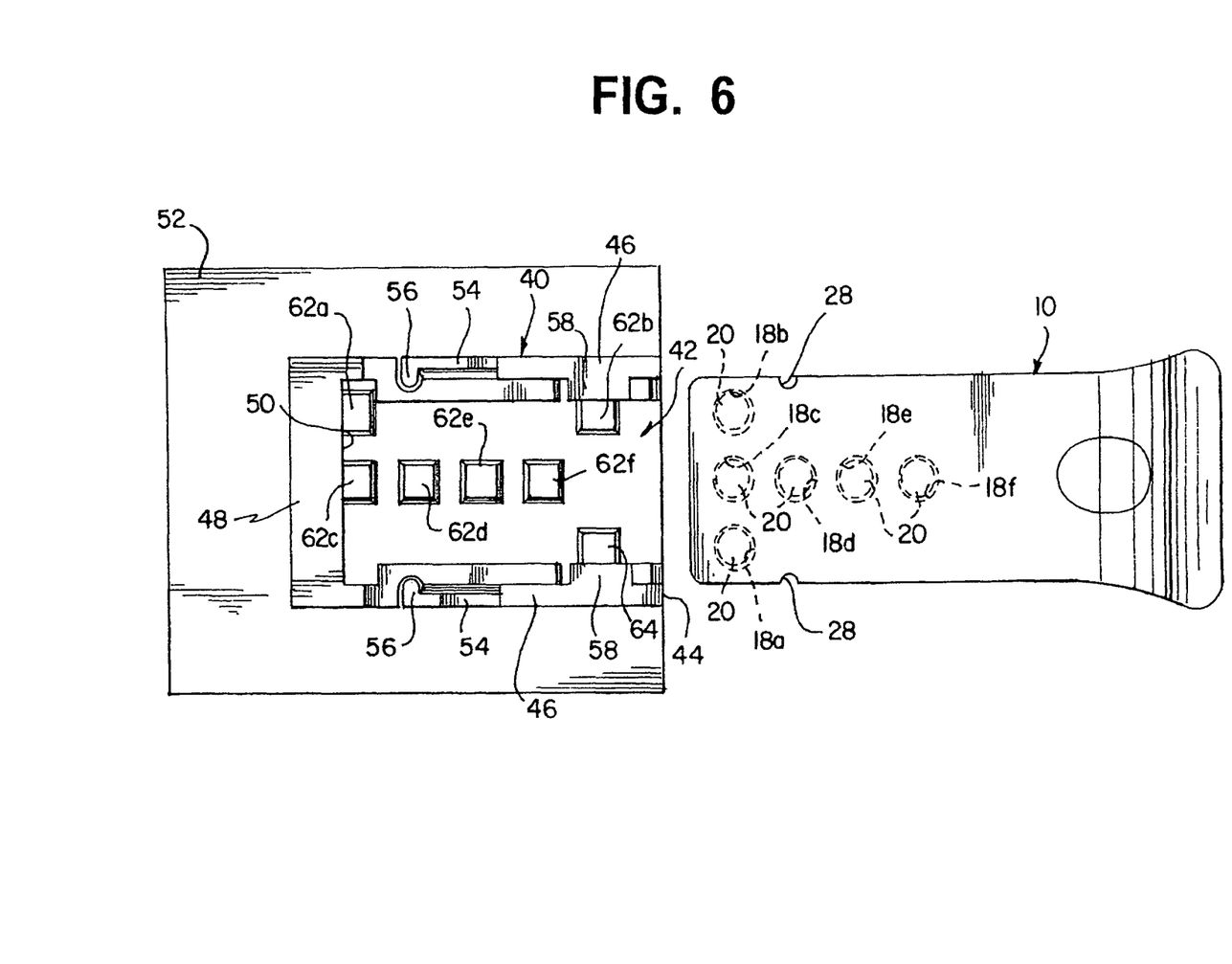
FIG. 6 is a top plan view of the key receiver of FIG. 2 showing in phantom lines the relative position of the magnets located within the key card and Hall-effect sensors located on the printed circuit board and showing the key card in a fully removed position, according to the first embodiment of the invention.
Figure 7:
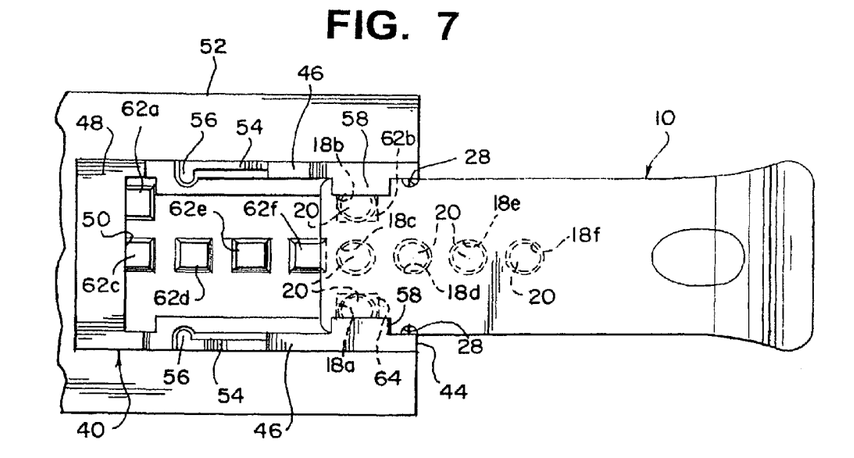
FIG. 7 is a top plan view of the key receiver of FIG. 2 showing in phantom lines the relative position of the magnets located within the key card and the Hall-effect sensors located on the printed circuit board and showing the key card in a "wake-up" inserted position, according to the first embodiment of the invention.
Figure 8:
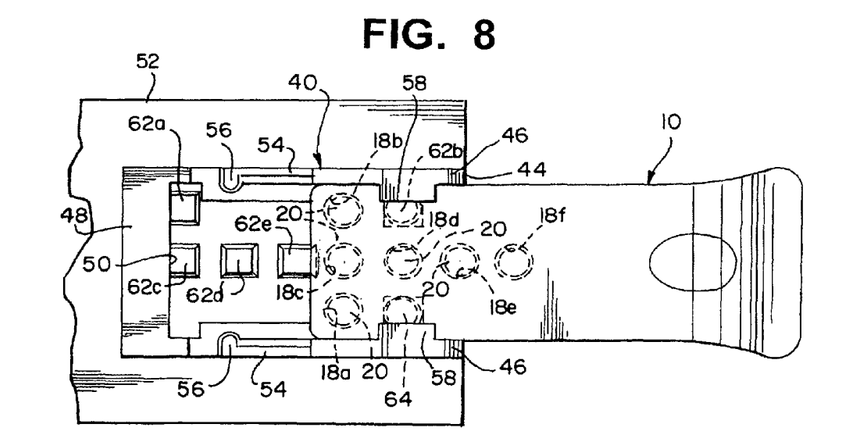
FIG. 8 is a top plan view of the key receiver of FIG. 2 showing in phantom lines the relative position of the magnets located within the key card and the Hall-effect sensors located on the printed circuit board and showing the key card in a first partially inserted position, according to the first embodiment of the invention.
Figure 9:
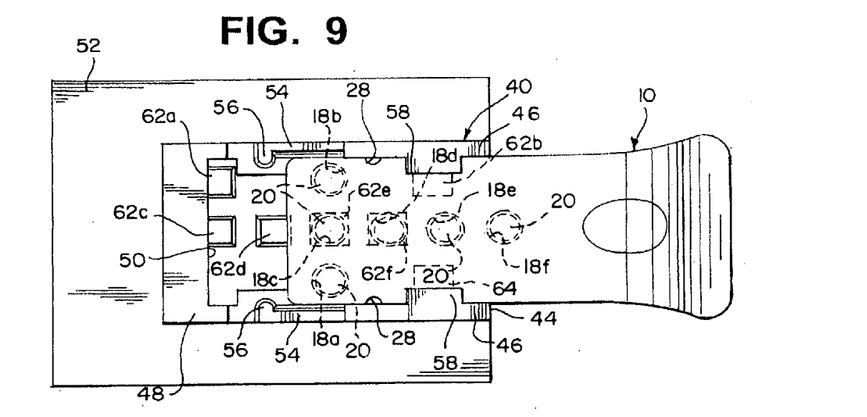
FIG. 9 is a top plan view of the key receiver of FIG. 2 showing in phantom lines the relative position of the magnets located within the key card and the Hall-effect sensors located on the printed circuit board and showing the key card in a second partially inserted position, according to the first embodiment of the invention.
Figure 10:
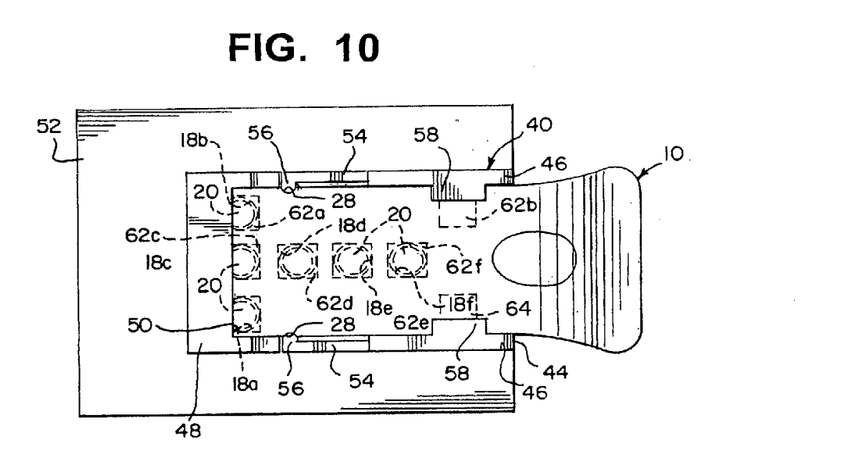
FIG. 10 is a top plan view of the key receiver of FIG. 2 showing in phantom lines the relative position of the magnets located within the key card and the Hall-effect sensors located on the printed circuit board and showing the key card in a fully inserted and locked position, according to the first embodiment of the invention.

Referring now to FIGS. 6-10, keycard 10 is shown being inserted into slot 42 from a fully removed position, shown in FIG. 6, to a fully inserted position, shown in FIG. 10.

According to the invention, a magnet 20 is always located in the two corner bore positions 18a and 18b, the front corners of the keycard 10. These two corner magnets 20 will be immediately detected, as keycard 10 is first inserted into slot 42 by start sensor 62b and sensor 64, which are positioned adjacent to slot 42 and which are aligned with one of the two corner magnets. In the example shown in FIGS. 1, 4, and 7, start sensor 62b aligns with the magnet located in corner bore 18b. Since a magnet 20 must be located within each corner bore 18a, 18b, then the system can still "read" the keycard regardless if the keycard is inserted upright or inverted. This early detection by start sensor 62b is used to "wake up" the onboard circuitry, which preferably was in sleep mode to conserve battery power. So-called "sleep modes" are used often in a variety of electronic components and are well known in the art.

As the keycard 10 continues to be pushed into channel 50 of key holder 40, it is preferred that the combination of the particular keycard 10 is not "read" by the three combination sensors 62c, 62d and 62f until stop sensor 62a reads the magnetic field of magnet 20 located in bore 18b (or 18a, if the card is inverted). The change in voltage of stop sensor 62a indicates to processor 68 that keycard 10 is fully inserted into channel 50 and combination bores 18c, 18e and 18f of keycard 10 are now aligned with their corresponding combination sensors 62c, 62d and 62f, respectively.

At this point, following appropriate software commands, processor 68 "reads" combination sensors 62c, 62d and 62f and uses logic high/low state readings of each combination sensor to determine which bores 18c 18e and 18f contain magnets 20. This information defines the particular combination of the inserted keycard 10. Appropriate software then instructs processor 68 to compare the key combination of the inserted keycard 10 with the four combinations stored in memory chip 74. Depending on the match, the software will allow the user access to only those modes of operation, functions, and displayed and stored data that are permitted to the particular combination of the inserted keycard 10. In other words, the arrangement of magnets 20 located on the keycard 10, within combination bores 18c, 18e and 18f effectively tells the processor and the device 60 if the user is a physician, a salesman, a technician or a factory assembly worker and as long as the keycard 10 remains in its fully inserted position within the channel 50 (as continuously verified by stop sensor 62a). Processor 68 will operate the device following the prescribed access and control assigned to that particular identified user.

Continuing with the example introduced earlier in this application, Applicants contemplate providing the assembly worker with the highest level of rights to operate the device. This is required so that during assembly all the required software calibration parameters and manufacturing initialization parameters may be utilized to ensure the device operates as intended. The technician and the salesman will be granted an intermediate level of access to certain software parameters. The physician will only be allowed access to the most restrictive level of rights to the software parameters, including access to select programmable parameters directly related to the patient and to the drug prescription. In this example, the physician will be denied any access to any calibration parameters or software used to adjust these calibration parameters since such actions are beyond the physician's level of need to operate the device. If access to such information and control were given to the physician, it is likely that the device would soon fail to operate or would operate inaccurately, placing the patient's health at risk. The levels of access to the particular users, such as the ones listed in the example above are provided as required by the particular user to enable that user to successfully perform the required task without risking the patient's health.

The onboard software preferably instructs processor 68 to continually interrogate and read combination sensors 62c, 62d and 62f and stop sensor 62a until stop sensor 62a detects that keycard 10 is being removed, at which point, processor causes the device to shut down or enter into a predetermined operating mode, eventually returning to sleep mode, after a prescribed time period has passed.

What is claimed is:

1. An access system for controlling access of a user to one of at least two unique operative modes of an electronic device for communicating with an implantable medical device, said access system comprising:
   a portable keycard of said user having at least a first magnet embedded therein, said first magnet being located at a first predetermined location within said keycard;
   an electronic device comprising:
      a housing having an external surface and an interior chamber, said external surface including a channel which is sized and shaped to selectively receive said keycard to a fully inserted position;

a sensing circuit disposed within said interior chamber, said sensing circuit including a first Hall-effect transducer positioned adjacent to said channel so that said first magnet of said keycard aligns with said first Hall-effect transducer when said keycard is located at said fully inserted position within said channel, at which point said first Hall-effect transducer generates a first output signal; and a processing circuit disposed within said interior chamber, said processing circuit being electrically connected to said sensing circuit and said processing circuit allowing said user access to said one of at least two unique operative modes in response to receipt of said first output signal.

2. The access system according to claim 1, wherein said sensing circuit includes a second Hall-effect transducer positioned remotely with respect to said first magnet of said keycard when said keycard resides at said fully inserted position, said second Hall-effect transducer being adapted to detect remote magnetic fields due to incoming stray magnetic fields entering the electronic device, said second Hall-effect transducer generating a second output signal in response to said remote magnetic fields being detected.

3. The access system according to claim 2, wherein said processing circuit denies said user access to said one of at least two unique operative modes in response to receipt of said second output signal, regardless of said first output signal.

4. The access system according to claim 1, wherein said housing external surface includes a slot, said keycard includes a front edge which is initially inserted within said slot of said housing and further including an embedded second magnet positioned along said front edge.

5. The access system according to claim 4, wherein said sensing circuit includes a third Hall-effect transducer positioned adjacent said slot of said housing so that said second magnet positioned along said front edge of said keycard moves into momentary alignment with said third Hall-effect transducer during insertion of said keycard into said slot and channel, said third Hall-effect transducer generating a third output signal in response to detecting said second magnet.

6. The access system according to claim 5, further including a power-conserving circuit which is electrically connected to said processing circuit and said sensing circuit and wherein power to at least one electronic component of said processing circuit and said sensing circuit is selectively controlled between a fully-powered condition and a sleep-mode condition wherein said at least one component receives reduced power.

7. The access system according to claim 6, wherein said power-conserving circuit operates in response to a predetermined time period elapsing as determined by said processing circuit.

8. The access system according to claim 6, wherein said power-conserving circuit switches said at least one electronic component from said sleep-mode to said fully-powered mode in response to receipt of said third output signal.

9. The access system according to claim 8, wherein said at least one electronic component is said first Hall-effect transducer.

10. The access system according to claim 9, wherein said second Hall-effect transducer remains in said fully-powered condition.

11. The access system according to claim 5, wherein said sensing circuit includes a fourth Hall-effect transducer positioned adjacent said channel of said housing so that said second magnet positioned along said front edge of said keycard moves into alignment with said fourth Hall-effect transducer when said keycard reaches said fully inserted position within said channel, said fourth Hall-effect transducer generating a fourth output signal in response to detecting said second magnet.

12. The access system according to claim 11, wherein said processing circuit provides continuous operation of said electronic device at said at least one operative modes in response to said fourth output signal remaining unchanged.

13. The access system according to claim 12, wherein said processing circuit ends operation of said electronic device in response to a change of said fourth output signal indicating said second magnet no longer residing adjacent to said fourth Hall-effect transducer.

14. The access system according to claim 1, wherein said output signal represents the identity of said keycard and wherein said access system further comprises an electronic memory electrically connected to said processing circuit, said memory including data of at least two unique keycard identities and said corresponding at least two operative modes.

15. The access system according to claim 14, wherein said processing circuit compares said identity of said inserted keycard with said at least two unique keycard identities stored in said memory and provides selective access to operate said electronic device in said corresponding at least two operative modes in response to a positive comparison.

16. The access system according to claim 1, wherein the first magnet and first Hall-effect transducer being exclusively for detecting full insertion of said keycard within said channel and not associated with determining access to said one of at least two unique operative mode.

17. An electronic control device for communicating with an implantable medical device, said control device being operable in at least two unique modes of operation, as determined by a portable keycard, said control device comprising:

a housing having an external surface and an interior chamber, said external surface including a channel which is sized and shaped to selectively receive said keycard to a fully inserted position, said keycard having at least a first magnet embedded therein, said first magnet being located at a first predetermined location within said keycard;

a sensing circuit disposed within said interior chamber, said sensing circuit including a first Hall-effect transducer positioned adjacent to said channel so that said first magnet of said keycard aligns with said first Hall-effect transducer when said keycard is located at said fully inserted position within said channel, at which point said first Hall-effect transducer generates a first output signal; and a processing circuit disposed within said interior chamber, said processing circuit being electrically connected to said sensing circuit and said processing circuit allowing said control device to operate in one of said at least two unique modes of operation in response to receipt of said first output signal.

18. The electronic control device according to claim 17, wherein said sensing circuit includes a second Hall-effect transducer positioned remotely with respect to said first magnet of said keycard when said keycard resides at said fully inserted position, said second Hall-effect transducer being adapted to detect remote magnetic fields due to incoming stray magnetic fields entering the electronic device, said second Hall-effect transducer generating a second output signal in response to said remote magnetic fields being detected.

19. The electronic control device according to claim 18, wherein said processing circuit denies said user access to said one of at least two unique modes of operation in response to receipt of said second output signal, regardless of said first output signal.

20. The electronic control device according to claim 17, wherein said external surface of said housing includes a slot, said keycard includes a front edge which is initially inserted within said slot of said housing and further including an embedded second magnet positioned along said front edge.

21. The electronic control device according to claim 20, wherein said sensing circuit includes a third Hall-effect transducer positioned adjacent said slot of said housing so that said second magnet positioned along said front edge of said keycard moves into momentary alignment with said third Hall-effect transducer during insertion of said keycard into said slot and channel, said third Hall-effect transducer generating a third output signal in response to detecting said second magnet.

22. The electronic control device according to claim 21, further including a power-conserving circuit which is electrically connected to said processing circuit and said sensing circuit and wherein power to at least one electronic component of said processing circuit and said sensing circuit is selectively controlled between a fully-powered condition and a sleep-mode condition wherein said at least one component receives reduced power.

23. The electronic control device according to claim 22, wherein said power-conserving circuit operates in response to a predetermined time period elapsing as determined by said processing circuit.

24. The electronic control device according to claim 22, wherein said power-conserving circuit switches said at least one electronic component from said sleep-mode to said fully-powered condition in response to receipt of said third output signal.

25. The electronic control device according to claim 24, wherein said at least one electronic component is said first Hall-effect transducer.

26. The electronic control device according to claim 25, wherein said second Hall-effect transducer remains in said fully-powered condition.

27. The electronic control device according to claim 21, wherein said sensing circuit includes a fourth Hall-effect transducer positioned adjacent said channel of said housing so that said second magnet positioned along said front edge of said keycard moves into alignment with said fourth Hall-effect transducer when said keycard reaches said fully inserted position within said channel, said fourth Hall-effect transducer generating a fourth output signal in response to detecting said second magnet.

28. The electronic control device according to claim 27, wherein said processing circuit provides continuous operation of said electronic device at said at least one mode of operation in response to said fourth output signal remaining unchanged.

29. The electronic control device according to claim 28, wherein said processing circuit ends operation of said electronic device in response to a change of said fourth output signal indicating said second magnet no longer residing adjacent to said fourth Hall-effect transducer.

30. The electronic control device according to claim 17, wherein said output signal represents the identity of said keycard and wherein said access system further comprises an electronic memory electrically connected to said processing circuit, said memory including data of at least two unique keycard identities and said corresponding at least two modes of operation.

31. The electronic control device according to claim 30, wherein said processing circuit compares said identity of said inserted keycard with said at least two unique keycard identities stored in said memory and provides selective access to operate said electronic device in said corresponding at least two modes of operation in response to a positive comparison.

32. The electronic control device according to claim 17, wherein the first magnet and first Hall-effect transducer being exclusively for detecting full insertion of said keycard within said channel and not associated with determining access to said one of at least two unique operative modes.

\* \* \* \* \*